(12) United States Patent  
Kendrup

(10) Patent No.: US 9,775,905 B2
(45) Date of Patent: Oct. 3, 2017

(54) INTRAUTERINE DEVICE AND METHOD FOR REDUCING THE RATE OF DIFFUSION OF ACTIVE INGREDIENTS IN SAID DEVICE BY ADDING INERT PARTICULATES TO A POLYMERIC COATING

(71) Applicant: QPHARMA AB, Malmö (SE)

(72) Inventor: John Ingvar Feldtblad Kendrup, Oxie (SE)

(73) Assignee: QPharma AB, Malmö (SE)

( * ) Notice: Subject to any disclaimer, the term of this patent is extended or adjusted under 35 U.S.C. 154(b) by 10 days.

(21) Appl. No.: 14/766,121

(22) PCT Filed: Jan. 31, 2014

(86) PCT No.: PCT/IB2014/058696
§ 371 (c)(1),
(2) Date: Aug. 5, 2015

(87) PCT Pub. No.: WO2014/122563
PCT Pub. Date: Aug. 14, 2014

(65) Prior Publication Data
US 2015/0359890 A1 Dec. 17, 2015

(30) Foreign Application Priority Data
Feb. 8, 2013 (SE) ...................................... 1350155

(51) Int. Cl.
*A61F 6/14* (2006.01)
*A61K 31/57* (2006.01)
(Continued)

(52) U.S. Cl.
CPC ................ *A61K 47/02* (2013.01); *A61F 6/08* (2013.01); *A61F 6/142* (2013.01); *A61K 9/0039* (2013.01);
(Continued)

(58) Field of Classification Search
None
See application file for complete search history.

(56) References Cited

U.S. PATENT DOCUMENTS 4,069,307 A   1/1978  Higuchi et al.
4,292,965 A * 10/1981  Nash .................... A61K 9/0036
                                              128/833
(Continued)

FOREIGN PATENT DOCUMENTS

GB           1495735         12/1977
WO       WO 98/04220 A1      2/1998
WO       WO 2013/013172   *  1/2013  ............ A61M 31/00

OTHER PUBLICATIONS

International Search Report and Written Opinion, PCT/IB2014/058696, mailed Apr. 17, 2014.

*Primary Examiner* — Kevin S Orwig
(74) *Attorney, Agent, or Firm* — Winston & Strawn LLP

(57) ABSTRACT

An intrauterine device having at least one first pharmaceutically active ingredient and at least one first layer made of at least a first polymeric material, wherein between about 10 and about 60 v/v % of at least one particulate material is dispersed and/or incorporated in the first polymeric material. The presence of the particulate material will reduce the porosity of the polymer or otherwise obstruct the diffusion of the pharmaceutically active ingredient being released, thereby slowing its rate of release. In this way, it is possible to regulate the release rate and/or initial burst of the device, simply by adjusting the amount of particles/particulate material in the first layer, instead of having to adapt the size of the device to the desired release pattern, which requires expensive changes in production equipment and manufacturing processes.

25 Claims, 3 Drawing Sheets

(51) Int. Cl.
  *A61K 47/02*   (2006.01)
  *A61K 31/56*   (2006.01)
  *A61K 9/00*   (2006.01)
  *A61F 6/08*   (2006.01)
  *A61K 31/565*   (2006.01)
  *A61K 31/567*   (2006.01)
  *A61K 31/585*   (2006.01)
  *A61K 47/34*   (2017.01)

(52) U.S. Cl.
  CPC ............ *A61K 31/56* (2013.01); *A61K 31/565* (2013.01); *A61K 31/567* (2013.01); *A61K 31/57* (2013.01); *A61K 31/585* (2013.01); *A61K 47/34* (2013.01)

(56) References Cited

U.S. PATENT DOCUMENTS

| | | | |
|---|---|---|---|
| 4,601,714 A | | 7/1986 | Burnhill |
| 4,728,478 A | * | 3/1988 | Sacks ................. B32B 27/20 |
| | | | 264/108 |
| 2003/0092817 A1 | * | 5/2003 | Ruskin ................. A01G 25/02 |
| | | | 524/445 |
| 2004/0213846 A1 | * | 10/2004 | Greenblatt ............ A01N 25/08 |
| | | | 424/469 |
| 2006/0251824 A1 | * | 11/2006 | Boulais ................. A61L 27/28 |
| | | | 427/458 |
| 2009/0004246 A1 | | 1/2009 | Woolfson et al. |
| 2009/0202612 A1 | | 8/2009 | Ahmed et al. |

\* cited by examiner

INTRAUTERINE DEVICE AND METHOD FOR REDUCING THE RATE OF DIFFUSION OF ACTIVE INGREDIENTS IN SAID DEVICE BY ADDING INERT PARTICULATES TO A POLYMERIC COATING

This application is a 371 filing of International Patent Application PCT/IB2014/058696 filed Jan. 31, 2014, which claims the benefit of Swedish application no. 1350155-6 filed Feb. 8, 2013.

BACKGROUND

The present invention relates to a novel intrauterine device, a method of reducing the rate of diffusion of active ingredients in said intrauterine device and a method of manufacturing said intrauterine device.

Today intrauterine devices (IUDs) are one of the safest and most efficient contraception used worldwide. IUDs have also been used to administer spermicides, as well as a variety of locally or systematically active medicaments. The devices have provided several advantages since their use is controlled by the female; they allow for a better regulated dose of drug without attention by the user; and they avoid the destruction (by the intestine and by first pass through the liver) of an appreciable portion of the daily dosage of some drugs compared to their orally delivered counterparts.

The devices, including intravaginal rings (IVRs), are typically formed from biocompatible polymers and contain a drug released by diffusion through the polymer matrix. The devices may be inserted into the vaginal cavity and the drug may be absorbed by the surrounding body fluid through the vaginal tissue. In some IVR designs, the drug is uniformly dispersed or dissolved throughout the polymer matrix (monolithic system). In other designs, the drug may be confined to an inner core within the ring (reservoir system). Monolithic systems are expected to show Fickian diffusion-controlled drug release whereby the release rate decreases with time. Reservoir systems may exhibit a zero order release of loaded drugs.

Several IVRs are commercially available today. As examples can be mentioned the Estring®, Femring®, and Nuvaring®, each of which provide controlled and sustained release of steroid molecules over several days/weeks.

These known vaginal rings have been found particularly useful for the release of steroids, whose relatively small molecular size and substantially water-insoluble nature permit effective permeation through the hydrophobic elastomer, such that therapeutic concentrations may be readily achieved in the body.

However, diffusion in polymers is complex and is known to depend on a number of different factors, e.g. temperature, pressure, the manufacturing process, the solubility of the drug in the polymer, the surface area of the drug reservoir, the distance the drug must diffuse through the device to reach its surface and the molecular weight of the drug. Consequently, it remains a challenge to understand, predict and control the diffusion of small and large molecules in polymer systems. In this respect, the use of intrauterine devices to deliver drugs requires a design that regulates the release rate so as to reliably provide the user with the appropriate daily dose throughout the lifetime of the device.

In reservoir systems, the drug first partitions into the membrane from the reservoir and then diffuses to the other side of the membrane, where it is taken up by the receiving medium. While the reservoir is saturated, a constant concentration gradient of drug is maintained in the membrane, the rate of drug flux is constant, and zero order release is achieved. However, when drug concentration in the reservoir falls below saturation, the gradient across the membrane and the release rate both decay.

In reservoir systems, the purpose of the membrane is to mediate diffusion of drug. Because of their simplicity of mechanism and their ability to produce zero order release, reservoir systems would seem to be highly advantageous. However, reservoir systems can be difficult to fabricate reliably. Furthermore, pinhole defects and cracks in the membrane surrounding the reservoir, can lead to dose dumping, i.e. unintended, rapid drug release over a short period of time.

These problems are avoided in monolithic systems, in which drug is loaded directly into a polymer, which now acts as both a storage medium and a mediator of diffusion. Drug is typically loaded uniformly into monolithic devices, and the release is controlled by diffusion through the monolithic matrix material or through aqueous pores.

A problem with reservoir systems, and even more with monolithic devices, are that they typically exhibit an initial burst, i.e. excessive release of drug in the first few days. This may, depending on the concentration of released drug, cause undesirable side effects such as nausea or vomiting.

Several attempts have been made to overcome said problem, e.g as disclosed in WO9804220, which teaches a vaginal ring wherein the drug-containing core is positioned in a hollow internal channel of the device immediately prior to use. However, since it is difficult and troublesome to place the core in the ring in a reliable and safe manner, there is considerably production cost involved with said ring and there may be significant variations between different rings.

It is e.g. further believed that when some polymers are exposed to degradation agents such as oxygen and moisture, different polymer morphologies can develop. The differences in polymer morphology may cause the release rate of the active agent from the IUD to vary significantly. As a consequence of the inconsistent release rate profiles among different IVRs, clinical complications can occur. Additionally, when IVRs are stored, the release rate from the IVRs can change during the storage time, known as "release rate drift."

Furthermore, with passing time, release rate decreases, as drug that is deeper inside the monolith device must diffuse to the surface, since it has farther to travel, and the quadratic relation between distance and time becomes important. Since the geometric factor is essential in this respect, the effects can be minimised by using other geometric shapes or hemisphere monoliths to provide near-zero-order release, but such devices are neither easy nor inexpensive to fabricate.

As the amount of available drug decreases over time and with distance from the surface, the drug is often added in larger concentrations than actually required from a therapeutically point of view. The effect being that larger dosages of the active drug are released from the device. This will not only result in a higher production costs, but the user will also be subjected to higher dosages of the drug than is needed or desired.

Thus, there is a demand for a device and a method that reduces the variability of the release rate of active agents among IUDs, including IVRs, over time. Accordingly, there is a requirement for providing IUDs in which the known problems relating to complicated and expensive manufacturing processes, dose dumping and initial drug burst are eliminated, and which at the same time reduces the release rate of the drug in order to provide smaller IUD and/or IUD having a prolonged effective duration.

SUMMARY OF THE INVENTION

It is therefore a first aspect of the present invention to provide an IUD having a lower rate of diffusion of an active than the conventional devices.

It is a second aspect of the present invention to provide an IUD having a longer product life and which can be stored without providing an initial drug burst.

It is a third aspect of the present invention to provide an IUD having an overall weight and size, which is smaller than hitherto known.

It is a forth aspect of the present invention to provide an IUD that allows for maximum shelf life of the IUD.

In a fifth aspect according to the present invention is provided an IUD that is inexpensive to manufacture and is simple and reliable to use.

In a sixth aspect of the present invention is provided an IUD, which safely and effectively can be inserted into, and removed from, the vaginal cavity of the patient without causing discomfort.

The novel and unique features whereby these and further aspects are achieved according to the present invention is the fact that the intrauterine device comprises at least one first pharmaceutically active ingredient and at least one first layer made of at least one first polymeric material, and wherein between about 10 and about 60 v/v % of at least one particulate material is dispersed in and/or incorporated in said first polymeric material, and wherein the particulate material has a mean particle size of between 0.1 μm and 100 μm.

The diffusion of active ingredient(s) is linked to the physical properties of the polymer network and the interactions between the polymer and the active ingredient itself. Without being bound by theory, the inventor of the present invention believes that the presence of the particulate material in the first layer reduces the porosity and/or increases the tortuosity of the first layer, or otherwise obstructs the diffusion of the pharmaceutically active ingredient being released, thereby increasing the length of the path of the diffusion through the first polymeric material. This slows the release rate of the pharmaceutically active ingredient compared with the release rate from the same polymeric material having the same level of pharmaceutically active ingredient without the added particles. Furthermore, since some of the polymeric material has been replaced with the particulate material in the first layer, the amount of active ingredients, which can be dissolved in the polymeric material is highly reduced, providing a significantly lower initial burst.

In this way, it is possible to regulate the release rate and initial burst of the IUD, simply by adjusting the amount of particles/particulate material in the first layer, instead of as conventionally, where the size of the IUD is adapted to the desired release pattern, which requires expensive changes in production equipment and manufacturing processes.

In the context of the present invention the term IUD comprises any kind of intrauterine device (IUD), including but not limited to, intrauterine contraceptives (IUC), intrauterine systems (IUS) and intravaginal rings (IVR).

The IUDs of the present technology are accordingly capable of providing sustained delivery of one or more active ingredient in a substantially zero order release profile. By substantially zero order it is meant that a substantially constant amount of active ingredient is released over a given period of time. In some embodiments, the devices exhibit a substantially zero order release profile of the drug over at least one week, over at least one month, over more than a month or over more than one year.

It is important that the particulate material is dispersed and/or incorporated in the first polymeric material to an extent sufficient to reduce the diffusion rate of the pharmaceutically active ingredient through the first layer, while the reduced diffusion rate is still sufficient to maintain an effective level of active ingredient on the surface of the IUD. In this respect the inventor has discovered that these effects are achieved to the desired degree when between 10 and 60 v/v % of the particulate material are dispersed and/or incorporated in the first polymeric material. The v/v % refers to the volume ratio of the particulate material to the total volume of the first layer. In some embodiments it is however preferred that at least 15 v/v % of the particulate material is dispersed in the first polymer, even more preferred at least 20 v/v %, and even more preferred at least 25 v/v %. The exact volume/amount of the particulate material will also depend on the used polymer(s) and active ingredient(s). A person skilled in the art will based on the context of the present invention understand that it will be possible to control and/or adjust the diffusion rate in the first layer by varying the amount of the particulate material and/or by using various blends of different particulate materials i.e. different particles and particle sizes.

It must be noted that even though it is known to add particulate materials to polymeric materials, see e.g. GB 1495735 and U.S. Pat. No. 4,069,307, it is not known to add particulate materials to polymers in concentrations within the desired range according to the present invention. Small concentrations of particulate material i.e. concentrations below 10 v/v %, will have no or only a very limited effect on the release rate of the active ingredient, and are accordingly not relevant for the present invention. In this respect it is important to stress that volume percents cannot be converted to weights percents without knowledge of the densities and concentrations of the relevant materials and compositions. As an example can be mentioned that 20-w/w % barium sulphate in a silicone polymer, corresponds to 5.3 v/v %, under the proviso that the density of the barium sulphate is 4.5 g/cm$^3$ and the density of the silicone polymer is 1 g/cm$^3$.

The presence of between 10 and 60 v/v % of the particulate material in the first layer will not only lead to an increase in the mean path length the molecules of the active ingredients have to travel between two points in the first layer, but will also reduce the amount of active ingredients which can be dissolved in the polymeric material of the first layer. The latter is due to the fact that a part of the polymeric material has been replaced with the particulate material in the first layer, accordingly decreasing the release rate of the active ingredient in said first layer providing a reliable release rate and a lower initial burst. Accordingly, the first layer can be made smaller, providing a smaller product with a significant lower burst. The lower weight and size of the IUDs makes the production easier and less costly, and also makes the products easier and less expensive to handle and store.

It is important that the particulate materials do not interfere/interact with the polymeric material and/or active ingredient(s) so that the physical and/or chemical properties of the polymeric material(s) or active ingredient(s) is impaired negatively, i.e. by altering the properties such that the material cannot be used for the intended purpose, that is for an IUD.

As an example can be mentioned that materials which interacts with the polymer, such as silicon dioxide, also known as silica, will affect the polymeric material negatively. Silicone dioxide can be used to reinforce polymeric materials, e.g. silicones, wherein the silicone dioxide particles binds to the silicone and forms a strong 3-dimensional network on a molecular level. In this respect, the silicon dioxide can determine the silicones physical properties like viscosity (in the uncured state) and the tensile strength (in the cured state), and if the silica is used in the concentrations as in the present invention, i.e. between 10 and 60 v/v %, then the viscosity of the polymer will be increased to such a level that it cannot be used in e.g. an injection moulding process and/or the silicone will exhibit very different physical properties, properties which is not preferrably in the present invention.

Thus, in order to ensure that the particulate material does not interfere with neither the active ingredient(s) nor the polymeric material the particulate material is preferably an inert material. The dispersed particulate material is inert in the sense that it is non-reactive, i.e., the particles do not degrade or interact with the polymeric material or the active ingredient(s) so that the physical and/or chemical properties of the polymeric material(s) or active ingredient(s) is impaired negatively. The particulate material can be both inorganic and/or organic, and it is preferred that the material is a GRAS material, i.e. a material which is generally recognised as safe. The particulate material is otherwise compatible with the polymeric material sufficiently well to be dispersed and/or incorporated in the polymeric material and is capable of releasing the active ingredient at a controlled diffusion rate, which is appreciably slower when compared with a similar polymeric material not containing said particulate material. The slower release rate is still at a sufficient level to maintain the effectiveness of the released active material.

The problems known in the art of IUDs, e.g. a high initial drug burst, are therefore reduced and in some embodiments even eliminated. Since the release rate effectively is decreased it is possible to obtain an IUD having several advantages. It is e.g. possible to reduce the size of the IUD without affecting the delivered dosages of the active ingredient(s), thereby providing higher patient acceptance and material cost savings and accordingly also reducing manufacturing costs. Alternatively, a higher concentration of the active ingredient(s) can be added to IUD, providing an IUD with a longer duration.

The release profile of the IUDs can be evaluated by using one of the well-known dissolution apparatuses or other suitable techniques known to a person skilled in the art.

In order to effectively reduce the diffusion of the pharmaceutically active ingredient being released, the particulate material has a mean particle size of between 0.1 µm and 100 µm. In one embodiment according to the invention it is preferred that the mean particle size is between 0.5 µm-50 µm; more preferred between 1 µm-30 µm and even more preferred between 2 µm-20 µm, preferably around 10 µm. Particulate materials having a smaller size, e.g. fumed silica, precipitated silica, colloidal silica and the like, have in experiments proven to be less effective or even not effective at all, i.e. said materials have no or only very little effect on the release rate of the active ingredient(s). This is e.g. due to the fact that when particulate material having a size below 0.1 µm is combined with a polymeric material, this will result in a number of unwanted physical properties of the mixture. As one example can be mentioned that the viscosity of the mixture can be raised to levels which makes it useless for further processing, e.g. mixing, dosing and injection moulding.

As used herein, the term "particulate material" means any kind of material in particulate form, i.e. particles. The term "particle size" refers to a particles mean particle diameter. Particle size and particle size distribution can be measured using, for example, a Malvern laser scattering particle size analyser, or any other particle size measurement apparatus or technique known to persons skill in the art. As used herein, the term "particle diameter" relates to the mean particle size as obtained from laser scattering using volumetric measurement based on an approximate spherical shape of a particle. The present invention can comprise particles of any shape, e.g. semi-spherical, ellipsoidal, or cylindrical particles.

Examples of preferred inert material suitable in the present invention can be selected from the group comprising magnesium stearate, Betonies, talc, clay, calcium stearate, stearic acid, calcium sulphate, sodium stearyl fumarate, and combinations of one or more of said materials. Talc and clay have proven especially advantageous, since these not only provide the desired effect but they are also inexpensive resulting in lower manufacturing costs. However, other kinds of particulate material having the ability to decrease the release rate of active ingredient(s) are also contemplated within the scope of the present invention.

The particulate material can in principal have any three-dimensional shape as long as either the length of the path of the diffusion through the polymeric material in the first layer is increased and/or the amount of the active ingredient(s) which can be dissolved in the polymeric material in the first layer is reduced. However, in a preferred embodiment, the geometrical structure of the particulate material is chosen from a plate like structure, a flat structure and/or a layered structure, enabling the molecules of the at least one active ingredient to be contained within spaces between the flat particulate material. Other geometrical shapes providing the same benefits are however also preferred in the context of the present invention.

In a preferred embodiment the particulate material is surface-treated and/or modified in order to alter the three-dimensional shape and/or the hydrophobic properties and/or hydrophilic properties of the particulate material. Said surface treatment can be both physical treatments e.g. heat treatments, and/or chemical treatments, the only requirement being that the particulate material must not be altered in a way which makes the material degrade the polymeric material and the active ingredient(s).

In a preferred embodiment the at least one active ingredient is incorporated and/or dissolved at least one second layer optionally made of at least one second polymeric material. Said at least one first layer preferably at least partly encapsulate i.e. enclose, surround and/or cover, said second layer. Said second layer can in a preferred embodiment also comprise particulate material in a similar manner as the first layer, in order to obtain similar advantages.

Accordingly, the release of the active ingredient(s) to the surroundings is dependent upon permeation (i.e., molecular dissolution and subsequent diffusion) of the active ingredient(s) not only though the first layer but also through the second layer. In this way, both the second drug-containing layer and the first layer function as release rate controlling layers. In this way a very effective and inexpensive IUD is obtained, in which the active ingredient(s) are released in a more controlled manner than hitherto known.

In this respect it is preferred that the outer layer of the IUD according to the invention, is the first layer. In this way the first layer will function as a membrane. Said first layer will due to the particulate material provide a lower permeability than a second layer without particulate material. As discussed earlier the release rate decreases, as active ingredient(s) that is deeper inside the second layer must diffuse to the surface, since it has farther to travel, and the quadratic relation between distance and time becomes important. Using an outer layer with lower permeability as in the present embodiment, the impact of the longer travel distance decreases. Thereby is obtained an IUD where the release rate at steady state decreases much more slowly than with conventional IUDs in the art.

The thickness of the outer, first layer can be varied to further control the release rate of the active ingredient, however experiments have shown that since the first layer effectively is capable of decreasing the release rate of the active ingredient, the present invention have an intrinsically safe design against dose-dumping and initial burst, since the release rate of the active ingredient not only is controlled by the first layer but also by the second layer containing the active ingredient(s).

Accordingly, it will be possible to provide an IUD having a significant lower thickness of the first layer than hitherto known. In one embodiment the thickness of the first layer is between 0.05 mm and 3 mm. Said thickness can preferably be between 0.05 mm and 2 mm, more preferably between 0.1 mm and 2 mm and even more preferably between 0.2 mm and 1 mm, depending on the active ingredient(s) and the polymeric material.

The device of the present invention includes one or more active ingredient(s). Said active ingredients are preferably in a crystalline, dissolved or amorphous form, and can in principal be any kind of locally or systematically active medicament, which can be administrated vaginally.

It is however preferred that the at least one active ingredient is at least one steroid, e.g. contraceptive agent such as an estrogenic steroid, and/or a progestational steroid. In a preferred embodiment the active ingredient is a combination of estradiol with progestogen selected from the group consisting of levonorgestrel, d-1-norestrel and norethindrone, preferably levonorgestrel. However the steroids can also be selected in order to treat other conditions, e.g. vaginal atrophy and symptoms associated with menopause, e.g. hot flashes.

In a different embodiment the active ingredient may be a spermicides, an antimicrobial agent or an anti-viral agent. Such agents are well known in the art and will not be discussed in greater details in this application.

Irrespectively of the active ingredient or the intended use of the device, the IUD according to the invention is adapted to deliver pharmaceutically effective amounts of active ingredient(s). By "pharmaceutically effective," it is meant an amount, which is sufficient to affect the desired physiological or pharmacological change in the subject. This amount will vary depending upon such factors as the potency of the particular ingredient, the desired physiological or pharmacological effect, and the time span of the intended treatment. Those skilled in the arts will be able to determine the pharmaceutically effective amount for any given active ingredient(s) in accordance with standard procedures.

However, by utilizing the decreased relates rates obtained by the IUDs according to the present invention, the amounts/concentrations of the active ingredient(s) can either be reduced without compromising the reliability of the device, the size of the device can be reduced and/or the device can have an extended lifetime. In this respect it is noticeable, that even though vaginal rings have been used to deliver the contraceptive agent, ethinyl estradiol, an undesirable percentage of women who have used vaginal rings for this purpose have complained of nausea and vomiting, particularly from the first cycle of use of the rings due to an initial burst of steroid release. Using the unique design of the present invention, such initial busts are significantly reduced and in some cases even eliminated.

The polymeric materials used in the IUD of the present invention are preferably suitable for placement in the vaginal tract, i.e., they are non-toxic and non-absorbable in the patient. In this respect a variety of inert thermoset or thermoplastic elastomer are contemplated.

It is however preferred that the polymer material is a thermosetting elastomer, especially a silicone polymer (thermosetting type), as experiments have shown that these materials provides especially advantageously reduced release rates, and substantially no initial burst. Silicone elastomers, such as poly(dimethylsiloxane) are already used conventionally for IVRs and similar silicones are contemplated within the scope of the present invention.

However, in other embodiments the polymers can also be a thermoplastic polymer, which in principle can be any extrudable thermoplastic polymer material suitable for pharmaceutical use, such as ethylene-vinyl acetate (EVA) copolymers, low-density polyethylene, polyurethanes, and styrene-butadiene copolymers. In one embodiment, ethylene-vinyl acetate copolymer is used due to its excellent mechanical and physical properties.

Combinations of polymeric materials are also contemplated within the scope of the present invention.

The IUD according to the invention can have any conventional shape, the only requirement being that the IUD should be flexible enough to enable bending and insertion inside the vaginal cavity and rigid enough to withstand the expulsive forces of the vaginal musculature without causing abrasion to the vaginal epithelium.

In a preferred embodiment, the IUD of the present technology is an intravaginal ring (IVR). The dimensions of the IVR may vary depending upon the anatomy of the subject, the amount of drug to be delivered to the patient, the time over which the drug is to be delivered, the diffusion characteristics of the drug and other manufacturing considerations. In the context of the present invention the term intravaginal ring, also contemplates ring designs or structures, which have other shapes, e.g. polygonal shapes and/or wavy shapes, or where the structure is not a complete and/or closed circle/shape.

The design of the vaginal ring can within the scope of the present invention be any conventional design, e.g. either a "sandwich" or "core" vaginal ring design (also known as "shell" and "reservoir," respectively). The sandwich design consists of a second layer, i.e. a drug-loaded polymer layer (second layer) positioned between a nonmedicated inner central core and a nonmedicated outer first layer, i.e. the layer comprising the particulate material. The position of the drug-layer close to the surface ensures efficient delivery of drugs having poor polymer diffusion characteristics. In the core-type ring the second layer constitutes one or more central cores, i.e. drug-loaded polymer core(s), which is encapsulated by a drug-free first layer according to the invention, i.e. a layer comprising the particulate material.

When the IUD according to the invention comprises more than one active ingredient, said active ingredients can either be part of the same second layer, or the second layer can be dividing into several section, each of which comprises an individual active ingredient. Said design has the advantage that each section of the second layer can be manufactured independently of a different section, enabling use of different polymeric materials and accordingly different diffusion characteristics, in the individual sections. Furthermore, the respective active ingredient need not be completely compatible. Alternatively, or in combination, the IUD can comprise more than one second layers, each of which comprise an active ingredient, and optionally a suitable amount, e.g. between 10 and 60% v/v, of particulate material.

The active ingredient in one or more additional second layer(s) is preferably different from the active ingredient in another second layer. For example, the active ingredient in one second layer may be a contraceptive and the active ingredient in a different second layer may be an antiviral agent. However for some embodiment it can be desired to have the same active ingredient in several second layers, and wherein said layers comprise different amounts/concentrations of particulate material. In this way it is possible to obtain an IUD with a gradient of the active ingredient, and accordingly a different release profile. In a similar manner the polymeric material of the individual second layers need not be the same.

In a similar manner the IUD can comprising more than one first layer each of which comprises particulate material, preferably with varying degrees of particulate material. Such an embodiment ensures that the release of the active ingredient(s), can be regulated, reduced and/or delayed to a higher degree, by providing a gradient of particulate material over the respective first layers.

The first layer(s) and the layer(s) with active ingredient can within the scope of the present invention, be placed in any desired relationship, e.g. several first layers comprising particulate material can be placed next to (.e. overlaying) each other or be interrupted by one or more second layers comprising active ingredient(s).

The outer diameter of the IVRs may range, e.g., from about 45 mm to about 65 mm and the cross-sectional diameter of the IVRs may vary from about 1.5 mm to about 10 mm, preferably about 4 mm.

The present invention also relates to a method of manufacturing the IVRs according to the present invention.

Said method comprises injection moulding or extrusion of the at least one first layer. Preferably, the at least one second layer is formed simultaneously with said first layer. Alternatively, the first and second layers can be formed in separate injection moulding or extrusion steps. It is further preferred that the polymer of the first layer e.g. poly(dimethylsiloxane), is mixed with the particulate material(s) and optionally a polymerisation catalyst during the injection moulding or the extrusion step, as this will provide a very simple and inexpensive embodiment according to the invention. The formed layers are subsequently injected into ring shaped moulds, and allowed to cure for a period of time for a predetermined temperature. Injection moulding and extrusion are well known in the art and will not be discussed further in this application.

BRIEF DESCRIPTION OF THE DRAWINGS

The invention will be explained in greater detail below, describing only exemplary embodiments of the IUDs according to the invention

DETAILED DESCRIPTION OF THE INVENTION

The invention is described with the assumption that the IUD is a vaginal ring. However, this assumption is not to be construed as limiting, and the IUD can just as easily have a different structure/design, or be a different kind of IUD, e.g. a hormone spiral.

Figure 1:
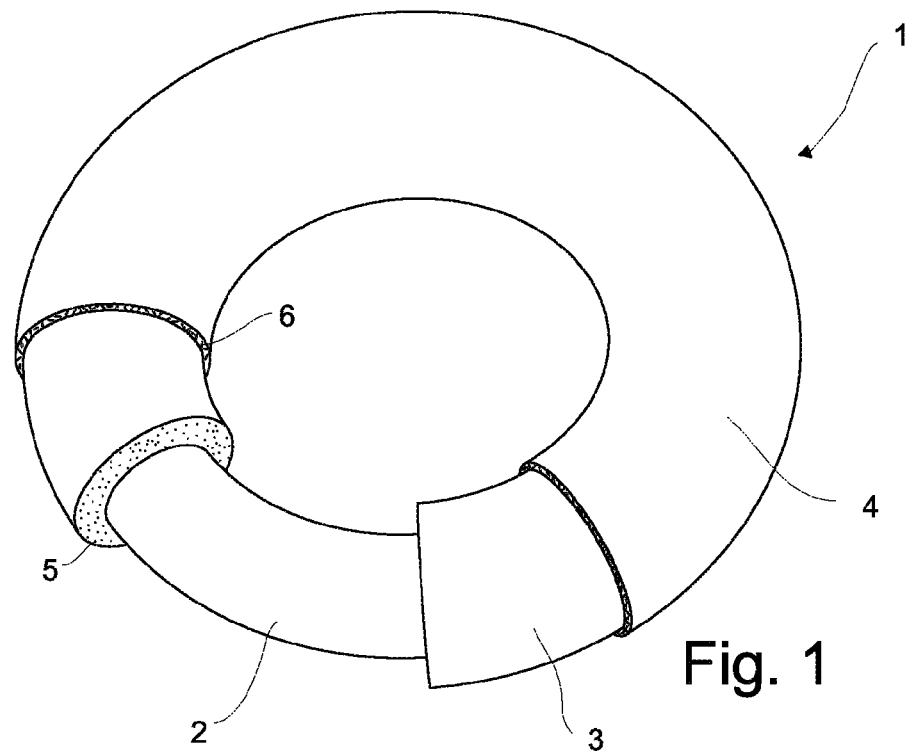
FIG. 1 shows a perspective view of a first embodiment of a vaginal ring according to the invention, having a shell design.

FIG. 1 shows a perspective view of a first embodiment of an intravaginal ring 1 according to the present invention having a shell design. Said ring comprises a core 2, a second layer 3 and a first layer 4 encapsulating the second layer. The core 2 is a thermoplastic polymer and each layer 3,4 is preferably made of an inert polymer, preferably a pharmaceutical acceptable silicone.

In the second layer 3 is dispersed and/or dissolved at least one pharmaceutically active ingredient 5 and in the first layer 4 is dispersed/incorporated between 10 and 60 v/v % of at least one particulate material 6.

Figure 2:
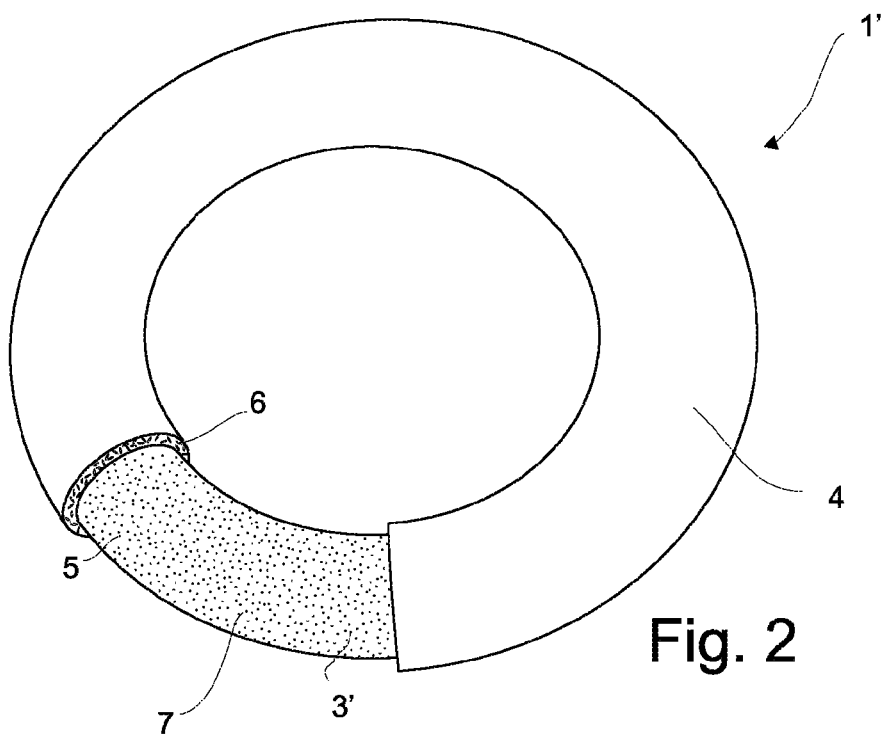
FIG. 2 shows a perspective view of a second embodiment of a vaginal ring according to the invention, having a reservoir design.

FIG. 2 shows a second embodiment of a vaginal ring according to the invention, having a reservoir design. In said embodiment the second layer 3', containing the active ingredient 5, constitutes a central core 7, i.e. a drug-loaded polymer core, which is encapsulated by the first layer 4, containing the particulate material 6, in a similar manner as in FIG. 1.

Figure 3:
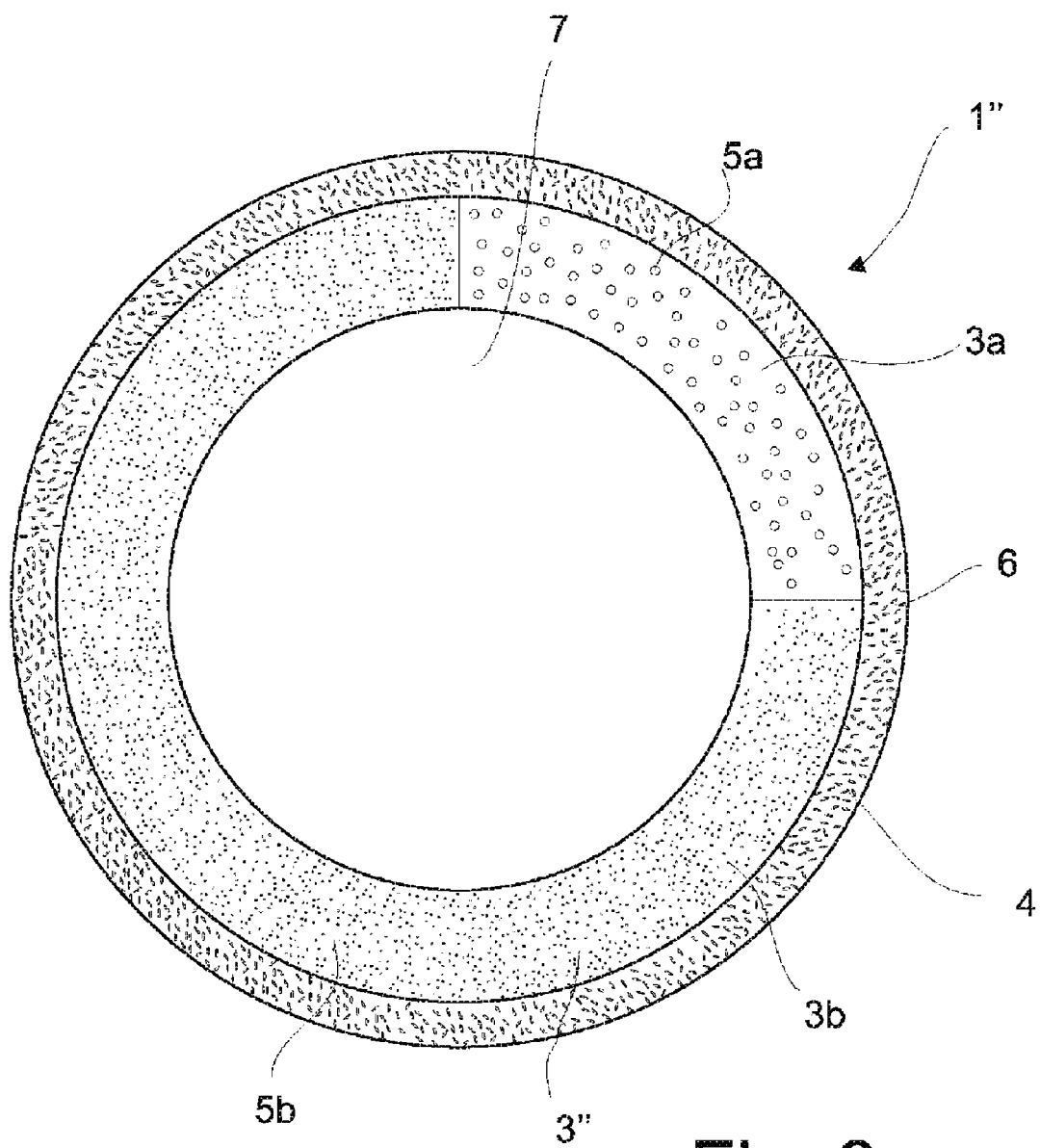
FIG. 3 shows a cross section view of a third embodiment of a vaginal ring according to the invention, having a reservoir design.

FIG. 3 shows a third embodiment 1", which is a variant of the embodiment shown in FIG. 1. For like parts same reference numbers are used. In said embodiment the second layer 3" has been divided into two section 3a, 3b, each of which comprises an individual active ingredient 5a, 5b. Said design has the advantage that each section 3a,3b of the second layer 3", can be manufactured independently, enabling use of different polymeric material with different properties, and accordingly different diffusion characteristics in the individual sections.

The presence of the particulate material 6 in the first layer of all embodiments reduces the porosity of the polymer or otherwise obstructs the diffusion of the pharmaceutically active ingredient 5 being released from the second layer 3, thereby increasing the length of the path of the diffusion through the polymer of the first layer. Furthermore, since some of the polymeric material has been replaced with the particulate material in the first layer 4, the amount of dissolved active ingredients, which can be dissolved in the polymeric material, has been reduced. Accordingly, build up of active ingredient in the first layer is difficult, simply since lower concentrations of active ingredient can be dissolved in the first layer.

In this way, it is possible not only to regulate the release rate of the IUD, simply by adjusting the amount of particles/particulate material in the first layer 4, but it is also possible to provide a more reliable release rate and a lower initial burst, compared with the release rate and initial burst from a similar IVR without the added particles 6 in the first layer 4.

The geometrical structure of the particulate material 6 is preferably a flat structure and/or a layered structure, enabling the molecules of the at least one active ingredient 5 to be contained within spaces between the flat particulate material. However, a person skilled in the art will understand that the particulate material in principal can have any three-dimensional shape as long as the length of the path of the diffusion through the first polymer is increased such that the release rate of active ingredient is reduced.

In a similar manner as for the first layer, the particulate material can be dispersed/incorporated in the second layer containing the active ingredient. Alternatively or in combination, the first layer can comprise one or more active ingredients.

The embodiments shown in the figures comprise only one first and one second layer, however a person skilled in the art will understand that several first and second layers are contemplated within the scope of the invention.

EXAMPLES

In order to evaluate if a particulate material having a mean particle size between 0.1 μm and 100 μm and incorporated in a concentration between 10 and 60 v/v % in a first layer had any effect on the release rate and/or initial burst of an active ingredient contained in a second layer, a number of samples was constructed. In all samples the first layer encapsulates the second layer. Accordingly, the first layer functions as a membrane and the second layer functions as a drug-containing core.

A conventional moulding technique was used for preparing the relevant samples. The first and second layers were formed in separate steps. The particulate material were mixed with the polymer of the first layer; and active ingredient were mixed with the polymer of the second layer. The ingredients of the respective layers were thoroughly mixed in a SpeedMixer DAC-150. The formed mixes were subsequently injected into appropriate moulds, and allowed to cure for a period of time using a predetermined temperature, depending on the polymer. For all samples the diameter of the core were 1 mm.

In vitro release of the active ingredient in the samples were conducted with a typical dissolution test for vaginal rings, the samples were submerged in a glass flask containing 250 ml water (example 1) or 400 ml water medium (example 2 and 3) subjected to shaking of 130 rpm at 37° C. Samples were withdrawn after appropriate time periods, and the concentration was determined with an HPLC method.

Example 1

In the present experiment the first layer was made of polydimethylsiloxane (obtainable from NuSil Technology LLC) with varying amounts of talc (obtainable from Imerys Talc) as particulate material. The used talc had a mean particle size of 19.3 μm determined by laser diffraction. The second layer was made of polydimethylsiloxane (obtainable from NuSil Technology LLC) having a concentration of 0.1 w/w % estradiol (obtainable from Sigma-Aldrich Co. LLC).

The first layer were cured at 130° C. The second layer containing the estradiol was cured at room temperature.

Five different samples were manufactured, two of which contained no particulate material, and three having increasing amounts of particulate material in the first layer.

The samples were analysed for in-vitro drug release using the dissolutions test described above, and the results are shown in table 1.

TABLE 1 in-vitro release of estradiol from the five samples.

| No. | Thickness of first layer (mm) | Amount of talc (w/w %) | Amount of talc (v/v %) | Estradiol (μg/24 hours) |
|---|---|---|---|---|
| I | 1.0 | 0 | 0 | 2.10 |
| II | 0.6 | 0 | 0 | 3.42 |
| III | 0.6 | 20 | 8.5 | 2.43 |
| IV | 0.6 | 40 | 20 | 1.38 |
| V | 0.6 | 60 | 36 | 0.79 |

Sample I and II resemble the prior art, i.e. IVRs not having any particulate material incorporated into the first layer. When comparing sample no. V (comprising 36 v/v % particulate material) with the control sample having similar thickness of the first layer, i.e. ring no. II, it is evident that the release rate had been decreased more than four times. It means that the first layer can be made four times thinner, yielding a smaller product with lower or no initial burst.

Example 2

In order to further investigate the impact of the concentration of the particulate material in relation to the thickness of the first layer, a number of additional samples were constructed using the method described above.

In the present experiment the first layer (membrane) were made of polydimethylsiloxane with different amounts of talc (obtainable from Imerys Talc) having varying mean particle sizes. The mean particle sizes determined by laser diffraction of the talc used, are as follow: pharma grade: 19.3 μm, M grade: 10.5 μm and UM grade: 3.6 μm.

The second layer (core) were made of polydimethylsiloxane. Said core had nine parts by weight of polydimethylsiloxane and one part by weight of ethinyl estradiol (obtainable from Bayer Pharma AG). (i.e. the core contains 10 w/w % ethinyl estradiol).

The polydimethylsiloxanes were cured at 70° C. for 15 minutes.

The used polydimethylsiloxanes (both core and membrane) are a MED5-6381 silicone, obtainable from NuSil Technology LLC, and has a low viscosity (~10,000 mPas). Said polydimethylsiloxane comprises a tin catalyzed cure system (condensation cure) and does not contain fumed silica.

Thirteen different samples were manufactured with this method, four of which contained no particulate material.

In order to evaluate the initial burst of active ingredient, i.e. the amount of released ingredient in the first day, the samples were stored at 25° C. and 60% RH in three weeks prior to analysis to allow the active ingredient to diffuse into the first layer (membrane).

The samples were analysed for in-vitro drug release using the dissolutions test described above, and the results are shown in table 2.

TABLE 2 in-vitro release of ethinyl estradiol from the samples, no 1-13.

| No. | Thickness of first layer (mm) | Particles | Particle size (μm) | Particles (w/w %) | Particles (v/v %) | Day 1 (μg/24 hours) | Day 2 (μg/24 hours) | Day 3 (μg/24 hours) | Day 8 (μg/24 hours) | Day 15 (μg/24 hours) |
|---|---|---|---|---|---|---|---|---|---|---|
| 1 | 0.25 | — | — | 0 | 0 | 204.4 | 163.7 | 158.9 | 152.9 | 121.9 |
| 2 | 0.5 | — | — | 0 | 0 | 93.2 | 77.1 | 79.1 | 80.5 | 73.0 |
| 3 | 1 | — | — | 0 | 0 | 90.3 | 51.3 | 49.6 | 49.9 | 45.5 |
| 4 | 2 | — | — | 0 | 0 | 134.4 | 47.8 | 46.3 | 30.6 | 27.9 |
| 5 | 0.25 | Talc P. | 19.3 | 40 | 20 | 88.2 | 59.1 | 62.3 | 68.5 | 62.8 |
| 6 | 0.5 | Talc P. | 19.3 | 40 | 20 | 84.0 | 43.3 | 40.5 | 40.2 | 39.3 |
| 7 | 1 | Talc P. | 19.3 | 40 | 20 | 72.6 | 28.6 | 26.1 | 22.5 | 22.0 |
| 8 | 0.25 | Talc P. | 19.3 | 60 | 36 | 40.9 | 28.8 | 32.5 | 36.3 | 31.6 |
| 9 | 0.5 | Talc P. | 19.3 | 60 | 36 | 28.1 | 17.2 | 16.5 | 17.2 | 17.1 |
| 10 | 1 | Talc P. | 19.3 | 60 | 36 | 24.9 | 9.6 | 8.3 | 10.3 | 9.8 |
| 11 | 0.5 | Talc P. M | 10.5 | 40 | 20 | 64.2 | 34.1 | 33.4 | 33.6 | 35.4 |
| 12 | 0.5 | Talc P. UM | 3.6 | 40 | 20 | 41.7 | 23.6 | 26.9 | 26.1 | 27.4 |
| 13 | — | Silica | 0.012 | 25.7 | 13.6 | — | — | — | — | — |

Release Rate

Samples no. 1 to 4 resembles the prior art, i.e. IVRs not having any particulate material incorporated into the first layer (membrane).

Similar to the findings in example 1, the release rate of ethinyl estradiol is decreased significantly when the particulate material is incorporated into a vaginal ring. Furthermore, the initial burst is higher for the prior art samples than for the sample according to the invention.

Figure 4:
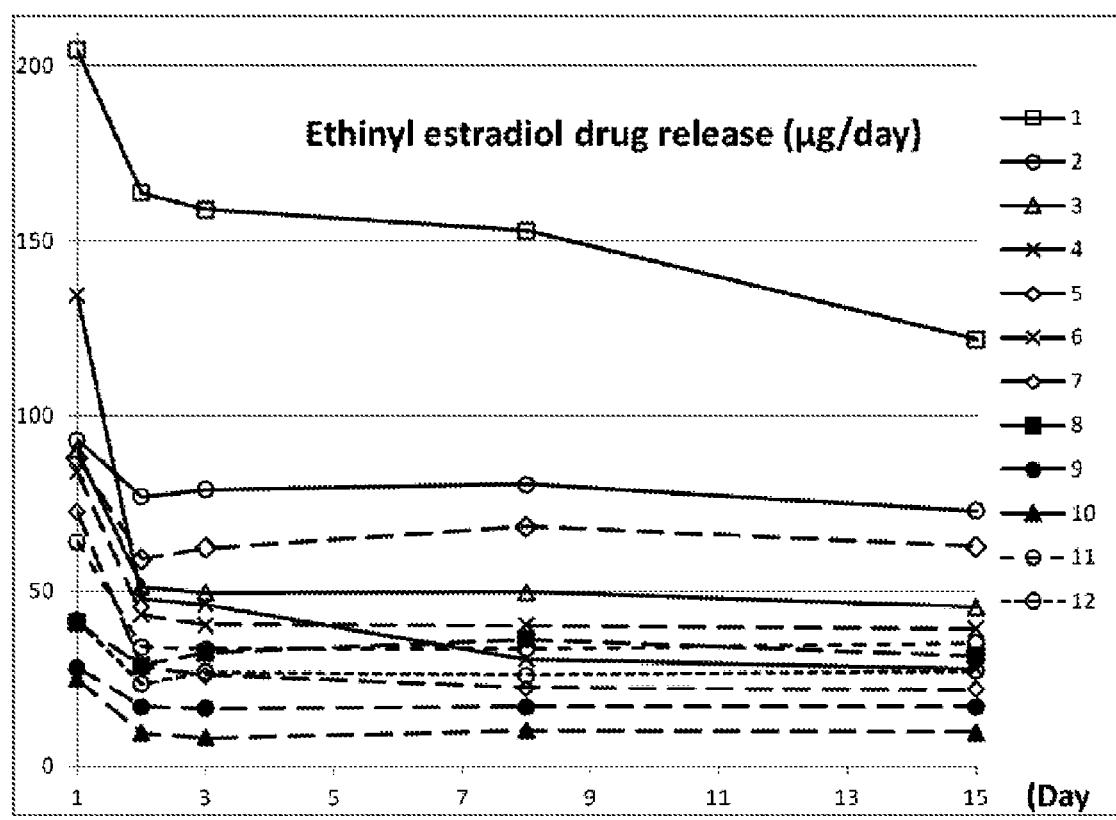
FIG. 4 depicts the release of ethinyl estradiol from the samples in example 2.

This is even more evident from FIG. 4 which is a graphical representation of the results in table 2, clearly showing that the initial burst is affected by both the size of the particles and the concentration in the first layer.

As an example can be mentioned that sample no. 4 (2 mm thickness of the first layer—no particles), releases 30.6 μg ethinyl estradiol per day at day 8. Said release rate can be compared to the release rate on day 8 of samples no. 12 (0.5 mm thickness of the first layer having a content of 20 v/v % talc with a mean particle size of 10.5 μm), having a release rate of 26.1 μg/day. However, if the same samples, i.e. samples no. 4, and 12 are compared for the initial burst at day 1, it is clear that the prior art (represented by sample no. 4) has a more than three times higher initial burst of 134.4 μg than the embodiment according to the invention (represented by sample no. 12), having a release rate of 41.7 μg/day, even though the first layer of the prior art sample is four times thicker than the first layer of the sample according to the invention.

Thus, the samples according to the invention comprising 20 v/v % talc in the first layer (e.g. const. no. 6 and 7) have a thinner first layer of between 0.5 and 1 mm and a significantly lower burst between 72.6-84.0 μg at day 1 compared to the prior art samples. The thinner membrane will result in a smaller product with lower cost (saves on raw material cost) but will also in many situations improve the patients' acceptance factor (a large vaginal ring is often perceived with discomfort). By increasing the amount of particulate material further to 36 v/v %, i.e. sample no. 8-9, an even thinner membrane and much lower burst of less of 40 μg/day (in-between 28.1 and 40.9 μg/day) can be achieved than for the prior art sample having an 134 μg/day drug release at day 1.

The examples further showed that the mean particle size of the particulate material had great impact on the viscosity of the talc and silicone mix and it also had an impact on the drug release rate, both at day 8 and on the initial burst at day 1. Comparing sample no. 6, 11 and 12, having same thickness of the first layer, but having different mean particles sizes of the particulate material, it is clear that the drug release which at day 8 was 40.2 μg/day with the large particle size (19.3 μm), decreased to 33.6 μg/day with the medium particle size (10.5 μm) and decreased further to 26.1 μg/day with the small particle size (3.6 μm).

Thus, it can be concluded that the initial burst also was affected by the particle size, whereby the initial burst decreased with decreasing particle size.

Viscosity During Mixing

Traditional injection molding equipment and techniques are intended to accommodate materials which can be melted to yield low viscosities. It is commonly understood that materials having a viscosity greater than about 8 kilopoise, including materials, e.g. silicone, with a degree of fill greater than about 40% by volumen, are unsatisfactory to process.

During the manufacturing of the samples no. 1-13 it was noted that when the particulate material was added to the polymer, the viscosity of the mixture of particulate material and polymeric material increased.

For sample no. 5-7 with 20 v/v % talc with large particle size (19.3 μm) a moderate visual increase in viscosity as observed. For sample no. 8-10 with 36 v/v % talc with large particle size (19.3 μm) a high increase in viscosity was observed, but it was still possible to use the mixture for injection molding. Example 11 with 20 v/v % talc with medium particle size (10.5 μm) gets a significant visual increase in viscosity but it was still possible to use the mixture for injection moulding. Sample no. 12 with 40 w/w % talc with small particle size was very similar to example 8-10 in respect of viscosity. Thus the talc did not alter the physical and/or chemical properties of the polymeric material(s) or active ingredient(s) negatively, i.e. the properties of the polymer was not altered to such an extend that the polymeric material cannot be processed and/or used for the intended purpose, i.e. as a IUD.

In sample no. 13; 40 w/w % silica (fumed silica) was attempted to be mixed into the silicone polymer. Said silica had a particle size of 0.012 μm and was obtainable from Wacker Chemie AG. When 25.7 w/w % (~13.6 v/v %) was added to the polymer, the attempt was haltered since the mix became too stiff to continue mixing. Thus, it is clear that trying to add high concentrations of silica, negatively affected the physical properties of the polymer, thereby making it unsuitable for further processing, e.g. for injection moulding, and thereby accordingly also unsuitable for use as an intrauterine device. Thus, that particulate material having a size below 0.1 µm, is not suitable as a particulate material in the present invention.

Example 3

Six additional samples were made, using the method described above, to further demonstrate the impact of the size of the particulate material added to the first layer (membrane), in the form of talc (particle size above 0.1 µm) and/or fumed silica (particle size below 0.1 µm).

The samples each contain a second layer in the form of a core. Said core contains three parts by weight of MED-4286 silicone and one part by weight of drospirenone (obtainable from Sterling S.p.A.) (i.e. the core contains 25 w/w % drospirenone). Said silicone does not comprise fumed silica.

The samples each comprises a first layer made of different silicones. In all samples the first layer had a thickness of 0.5 mm and had different amounts of talc (obtainable from Imerys Talc) and/or different amounts of fumed silica (silica). The mean particle sizes of the talc used, as determined by laser diffraction, were: Pharma grades: 19.3 µm; M grade: 10.5 µm and UM grade: 3.6 µm. The fumed silica had a particle size of 0.012 µm and was obtainable from Wacker Chemie AG.

The used silicones are all obtainable from NuSil Technology LLC, and were cured from 90 to 130° C. for 10 minutes.

In order to evaluate the initial burst of active ingredient, i.e. the amount of released ingredient in the first day, the samples were stored under room conditions for three weeks prior to analysis to allow the active ingredient to diffuse into the first layer.

The samples were analysed for in-vitro drug release using the dissolutions test described above, and the results can be seen in table 3.

The particle size of the added particles is relevant. Too small particle size causes a stiff mix already at modest concentrations. It is possible to choose a particle size that benefits the imperative. The use of large particle size facilitates high loading. The talc with approx. 10 µm particles size has a favorable balance. Said size has e.g. shown a soft and smooth mix with thixotropic behavior that counteract potential dripping and segregation with a loading of 20 v/v %.

From example 2 and 3 it can be concluded that particulate material, such as fumed silica, having a particle size smaller than about 0.1 µm (medium particle size determined by laser scattering) is not suitable for the present invention. The net effect of adding silica (particles which are smaller than 0.1 µm) on drug release is neglectable, and is likely a consequence of the high surface area of small particles that cause strong interactions with the silicones' physical properties, i.e. the uncured silicone becomes too stiff if the silicone is not adjusted to accommodate the silica. Test 15 and 16 use silicone that are adjusted to accommodate silica and does not show slower drug release compared to the test 14 that do not contain silica, accordingly it is important the particles have a mean particles size above 0.1 µm, preferably even higher.

It is furthermore evident from the above examples that the release rate is decreased significantly when the particulate material is incorporated into a first layer of a vaginal ring. Comparing prior art samples, i.e. samples having no particulate material in the first layer, with samples according to the invention, i.e. samples having particulate material in the first layer, it is evident that the release rate is significantly decreased.

This means that the first layer can be made thinner, yielding a smaller product with lower or no initial burst. Consequently, the manufacturing costs associated with IVRs according to the invention are considerably reduced and the user acceptability is highly increased.

TABLE 3 in-vitro release of drospirenone for the samples no. 14-19.

| No. | Silicone of first layer | Particles | Particle size (µm) | Particles (w/w %) | Particles (v/v %) | Day 1 (µg/24 hours) | Day 3 (µg/24 hours) | Day 3 (µg/24 hours) | Day 8 (µg/24 hours) | Day 15 (µg/24 hours) |
|---|---|---|---|---|---|---|---|---|---|---|
| 14 | MED-6010 (0 v/v % silica) | — | — | 0 | 0 | 352 | 331 | 360 | 375 | 372 |
| 15 | MED-4917 (13 v/v % silica) | — | — | 0 | 0 | 483 | 397 | 406 | 417 | 409 |
| 16 | MED4-4420 (10 v/v % silica) | — | — | 0 | 0 | 438 | 370 | 401 | 419 | 427 |
| 17 | MED4-4420 (10 v/v % silica) | Talc P. | 19.3 | 40 | 20 | 186 | 161 | 168 | 181 | 188 |
| 18 | MED4-4420 (10 v/v % silica) | Talc P. M | 10.5 | 40 | 20 | 181 | 148 | 152 | 168 | 170 |
| 19 | MED4-4420 (10 v/v % silica) | Talc P. UM | 3.6 | 40 | 20 | 194 | 160 | 161 | 175 | 168 |

By comparing sample no. 14-16 with samples no. 17-19, it is evident that adding talc to the silicone polymers significantly lowered the drug release rate at day 8. It is also clear that the amount of fumed silica in the silicone polymers does not substantially decrease the drug release rate, thus it is clear that the fumed silica has no significant effect on the release rate, this is due to the fact that fumed silica has a mean particle size of 0.012 µm, which is below 0.1 µm.

It is furthermore clear that both the initial burst and release rate of active ingredient and was smaller when talc was added to the first layer, compared to the samples without talc.

The IUD according to the invention has a simple and inexpensive design, and can therefore be used equally well both privately and in medical or hospital facilities.

Modifications and combinations of the above principles and designs are foreseen within the scope of the present invention.

What is claimed is:

1. An intrauterine device comprising at least one first pharmaceutically active ingredient and at least one first layer made of at least a first polymeric material, wherein between 10 and 60 v/v % of at least one particulate material is dispersed and/or incorporated in said first polymeric material, and wherein the particulate material is inert and has semi-spherical, ellipsoidal, or cylindrical shaped particles having a mean particle diameter of between 3.6 μm and 100 μm as measured by laser scattering using volumetric measurements based on an approximately spherical particle shape.

2. An intrauterine device according to claim 1, wherein the at least one particulate material is an inert inorganic or organic material.

3. An intrauterine device according to claim 1, wherein the at least one particulate material has a mean particle size of no greater than 50 μm; no greater than 30 μm, no greater than 20 μm, or 10 μm.

4. An intrauterine device according to claim 1, wherein the at least one particulate material is selected from the group comprising magnesium stearate, bentonite, talc, clay, calcium stearate, stearic acid, sodium stearyl fumarate and calcium sulphate.

5. An intrauterine device according to claim 1, wherein the at least one particulate material is talc.

6. An intrauterine device according to claim 1, where the at least one particulate material is surface-treated and/or modified to alter the three-dimensional shape or the hydrophilic/hydrophobic properties of the material.

7. An intrauterine device according to claim 1, wherein the thickness of the at least one first layer is between 0.05 mm and 3 mm, between 0.05 mm and 2 mm, between 0.1 mm and 2 mm or between 0.2 mm and 1 mm.

8. An intrauterine device according to claim 1, wherein an outer layer of the intrauterine device is the at least one first layer.

9. An intrauterine device according to claim 1, wherein the at least one pharmaceutically active ingredient is incorporated/dissolved in at least one second layer which may be made of at least one second polymeric material, and wherein said at least one first layer at least partly encapsulates said second layer.

10. An intrauterine device according to claim 9, wherein said at least one second layer is divided into sections, each of which comprises an individual active ingredient.

11. An intrauterine device according to claim 9, wherein said at least one first layer does not contain any pharmaceutically active ingredient(s).

12. An intrauterine device according to claim 9, which further comprises a central inert core that does not contain any active ingredient, and wherein said at least one second layer at least partly encapsulates the core, and said at least one first layer at least partly encapsulates said second layer.

13. An intrauterine device according to claim 9, wherein the at least first polymeric material of the first and/or second layer, and optionally the core, is at least one inert thermoset or thermoplastic elastomer.

14. An intrauterine device according to claim 12, wherein the core is made of a thermoplastic polymer, and the first and second polymeric material of the first and second layers respectively, are a thermoset elastomer or silicone.

15. An intrauterine device according to claim 13, wherein the thermoset elastomer is a pharmaceutically acceptable silicone or polydimethylsiloxane.

16. An intrauterine device according to claim 1, wherein the at least one active ingredient is at least one contraceptive agent, an estrogenic steroid, or a progestational steroid.

17. An intrauterine device according to claim 1, wherein the at least one active ingredient is at least one spermicide, an antimicrobial agent or an anti-viral agent.

18. An intrauterine device according to claim 1, which is a vaginal ring.

19. A method for reducing the rate of diffusion of an active ingredient though a polymeric material in an intrauterine device, wherein said method comprises incorporating at least one semi-spherical, ellipsoidal, or cylindrical shaped inert particulate material into said polymeric material, thus forming the intrauterine device of claim 1.

20. The method according to claim 19, wherein the particulate material has a mean particle size of between 3.6 μm-50 μm; between 5 μm-30 μm or between 10 μm-20 μm.

21. The method according to claim 19, wherein the at least one particulate material is selected from the group consisting of magnesium stearate, bentonite, talc, clay, calcium stearate, stearic acid and calcium sulphate.

22. A method of manufacturing an intravaginal ring according to claim 18, wherein the at least one first layer is prepared by injection moulding or by extrusion.

23. The method according to claim 22, wherein the at least one particulate material is selected from the group consisting of magnesium stearate, bentonite, talc, clay, calcium stearate, stearic acid and calcium sulphate.

24. The method according to claim 22, wherein the at least one semi-spherical, ellipsoidal, or cylindrical shaped inert particulate material is dispersed, dissolved and/or incorporated in the at least first polymeric material during the injection moulding or extrusion step.

25. The method according to claim 22, wherein the intravaginal ring further comprises at least one second layer and/or an inert core, and wherein said first layer and said second layer and/or said core is formed simultaneously or separately.

* * * * *